US009504387B2

(12) United States Patent
Alonsoperez Lanza (10) Patent No.: US 9,504,387 B2
(45) Date of Patent: Nov. 29, 2016

(54) DEVICE AND METHOD FOR THE EARLY DETECTION OF CATTLE PHYSIOLOGICAL VARIABLES AND LOCATION IN A REMOTE AND AUTONOMOUS WAY

(71) Applicant: Maria Victoria Alonsoperez Lanza, Montevideo (UY)

(72) Inventor: Maria Victoria Alonsoperez Lanza, Montevideo (UY)

( * ) Notice: Subject to any disclaimer, the term of this patent is extended or adjusted under 35 U.S.C. 154(b) by 174 days.

(21) Appl. No.: 14/062,413

(22) Filed: Oct. 24, 2013

(65) Prior Publication Data

US 2014/0121558 A1    May 1, 2014

Related U.S. Application Data

(60) Provisional application No. 61/718,517, filed on Oct. 25, 2012.

(51) Int. Cl.
*A61B 5/01* (2006.01)
*A61B 5/00* (2006.01)
*A61B 5/11* (2006.01)

(52) U.S. Cl.
CPC ........... *A61B 5/0008* (2013.01); *A61B 5/0022* (2013.01); *A61B 5/1112* (2013.01); *A61B 2503/40* (2013.01)

(58) Field of Classification Search
CPC ................. A61B 5/0008; A61B 5/01–5/015; A61D 17/002; A01K 11/006–11/008
USPC ..................... 119/858–859; 340/573.1–573.4
See application file for complete search history.

(56) References Cited

U.S. PATENT DOCUMENTS

| | | | | |
|---|---|---|---|---|
| 7,335,168 B2* | 2/2008 | Rugg | | A61B 5/1113 119/712 |
| 7,602,302 B2* | 10/2009 | Hokuf | | A01K 11/008 340/539.13 |
| 8,115,621 B2* | 2/2012 | Rajala | | G01S 1/042 340/539.11 |
| 8,438,999 B2* | 5/2013 | Hardi | | A01K 15/021 119/718 |
| 8,866,605 B2* | 10/2014 | Gibson | | A01K 11/006 340/539.1 |
| 2002/0010390 A1* | 1/2002 | Guice | | A01K 11/008 600/300 |
| 2004/0074448 A1 | 4/2004 | Bunt et al. | | |
| 2009/0058730 A1* | 3/2009 | Geissler et al. | | 342/450 |
| 2010/0030036 A1* | 2/2010 | Mottram et al. | | 600/301 |
| 2013/0014706 A1* | 1/2013 | Menkes | | A61D 13/00 119/859 |
| 2013/0285815 A1* | 10/2013 | Jones, II | | 340/573.3 |

FOREIGN PATENT DOCUMENTS

| | | |
|---|---|---|
| BE | 1015962 A7 | 12/2005 |
| EP | 2446855 A1 | 5/2012 |
| WO | WO-2008/138076 A2 | 11/2008 |

* cited by examiner

*Primary Examiner* — Devin Henson
*Assistant Examiner* — Audrey J Parker
(74) *Attorney, Agent, or Firm* — Muncy, Geissler, Olds & Lowe, P.C.

(57) ABSTRACT

A device or assortment of devices is provided for measuring temperature and/or other biological parameters, and locating cattle or other types of animals in a remote, continuous and autonomous way. This allows early detection of sickness and other biological states, especially epidemic outbursts or cattle rustling, thus facilitating the early reaction of owners and/or authorities.

14 Claims, 6 Drawing Sheets

DEVICE AND METHOD FOR THE EARLY DETECTION OF CATTLE PHYSIOLOGICAL VARIABLES AND LOCATION IN A REMOTE AND AUTONOMOUS WAY

CROSS-REFERENCE TO RELATED APPLICATIONS

This application claims priority of U.S. Provisional Application No. 61/718,517, filed on Oct. 25, 2012, under 35 U.S.C. §119(e), the entire contents of all of which are hereby incorporated by reference.

BACKGROUND OF THE INVENTION

Brief Summary of the Invention

In today's world, many problems can be solved thanks to technological advances and to the globalization of information. Nevertheless, there are still areas where those benefits have not arrived, especially if we consider the developing countries.

One of the main problems that affect developing countries is the disease that strikes one of their main productive assets: cattle. In this sense, the Foot-and-Mouth Disease (FMD or Aphthous Fever) is considered to be one of the biggest and most generalized problems in animal health. Entire regions, even including parts of several countries, have been greatly affected in their Gross Domestic Product by this disease and by the long duration of the decontamination process until the region's meat can be exportable again. There have been two examples in the South American region in the $21^{st}$ century. One was the 2001 crisis. When it occurred, it was one of the worst FMD epidemics in vast regions of South America, especially, in Uruguay in 100% of its territory. Since then, every once in a while an outbreak occurs, fortunately, not in Uruguay but in neighboring countries. Over two years ago there was an outbreak in the Republic of Paraguay that fortunately did not reach Uruguay.

The aforementioned is so important that in the recent years there were two editions of the Global Conference on Foot and Mouth Disease Control with the aim to reduce the global impact of the disease. Furthermore, the new president of the Mercosur (Argentina, Brazil, Paraguay, Uruguay and Venezuela) Meat Forum has set as his main objective to accomplish a Foot and Mouth Disease free Mercosur.

This work is based on the Uruguayan case because livestock products are the main source of export in a country where there are almost four heads of cattle per inhabitant, being this one of the highest ratios of cows to people in the world. I must stress, though, that the invention is valid for any other country. The case of Uruguay was taken due to its exceptional severity, for the abundance of available information, and for the losses in which the country incurred in overcoming the situation, including several years with its exports curtailed.

It is noteworthy that the Patents and Trademarks Office of Uruguay has submitted this application to the World Intellectual Property Organization (WIPO) Awards Program and on Jun. 14, 2013 this application was granted the WIPO Best Young Inventor Award. This project was already the winner of the International Telecommunication Union (ITU) Young Innovators Competition 2012 and was presented at the ITU Telecom World 2012 held in Dubai, United Arab Emirates.

It is therefore evident that both in Uruguay and all other farming countries there is a real need to stop these outbreaks as soon as they occur. I refer to stopping the disease when only one animal is sick, thus pre-empting the epidemic outburst. The problem is clearly identified and the solution cannot wait. The solution consists on measuring the animal's temperature in an autonomous, continuous and remote way. The temperature is measured through a subcutaneous chip that is implanted in the animal's retro auricular region. This chip is also a Radio Frequency Identification (RFID) transponder, which means that it can transmit its information to an RFID transceiver. The animal carries a collar containing an RFID transceiver, where the temperature measurement can be received and stored. Together with the RFID transceiver, there is a Global Positioning System (GPS) receiver (or any other system for geographical positioning) and a General Packet Radio Service (GPRS) modem (or any other data system transceiver). The board inside the collar is powered by a Lithium Polymer (LIPO) Battery or Lithium ion (Li-ion) battery charged by a solar cell located in the outside of the collar. When the animal's temperature exceeds a certain threshold, a text message (or the type that enables the technology available in the area) is sent to a server at the company's facilities, with the animal's identification, the temperature measurement and the coordinates of the animal's location. The content of the text message goes through a proprietary software program that immediately sets off an alarm. In a computer can be seen in real time on a map the location where the high temperature was detected, enabling fast decision making by a highly qualified veterinarian team.

All the power management system of the device makes it completely autonomous. This means that the device can send and receive information from remote areas without having to connect to the power grid and there is no need to have personnel manipulating the devices once placed in animals.

Another very useful application for my invention is to combat cattle rustling. This scourge, worse still in the border areas, is clearly an additional problem to be solved, and that my invention, by allowing the permanent location of livestock, helps combat. Since the RFID chip can be inserted subcutaneously and almost in any part of the animal, it is difficult to eliminate or even to detect. In this regard, I also intend to respond to a perceived need. Sickness and theft are not so independent factors: a stolen animal or herd necessarily travel long distances in a short time, many times crossing international borders, and spreading diseases in epidemic proportions if even one of them is sick. This is doubly so because stolen cattle are not precisely well cared for and are almost never under veterinarian control.

It could be the case that when stealing the animal the thief would cut the collar, therefore, a wire is also attached to the whole length of the collar so that if the collar is opened or cut an emergency message with the last position coordinates of the animal is sent to the company so appropriate action can be taken. A message is also immediately sent to the ranch administrator/owner.

The system can also detect if the coordinates of the animal's location correspond to a location outside of the ranch premises. In that case a message is also immediately sent to the ranch administrator.

The observable impact is huge and covers almost all the regions and countries in the world, especially the developing countries, where FMD has had its most extensive development and reaches dramatic levels, to the point that some regions have been depopulated of its cattle stock, either because of death due to infection or because of the "sanitary rifle" of the authorities. In any case, the damage to society and to the State is enormous and takes a lot of time to recover the international markets, being exports severely limited in both quantity and price.

This Project originated in Uruguay, a country that has suffered enormously from such consequences since the nineteenth century. The experience is deplorable because of the damages caused to the small rural producers, with repercussions across the whole society. The advantage of this work is that this type of project has the widest impact, benefiting not only farmers and private companies, but also countries and trading regions at its highest levels.

In addition, the impact of transparency is noteworthy because if the project is widespread and covers various countries the clarity and accessibility of the information are the foundations of the system. It has been documented that many times there are regions that try to hide the information the moment the outbreaks of FMD appear, with the purpose of protecting their economies (even though it is only for a very short time). This causes extensive damage to other nearby regions where the epidemic spreads, as well as to the credibility of future exports. Without a doubt, the development of this project will sooner or later become widespread because, as it has been seen in the history of telecommunications, they are one of the most significant elements in the contribution to transparency in all aspect of human activity.

Furthermore, it could also be the case that, because of great social interest, the Government (either Federal or State) will decide to assume the administration and operation of the project. In that case, the company would just provide the respective components. Although this case is not included in this document, it has been taken into account through a paragraph in the "Implementation Plan" Section. Also, the other use mentioned, the fight against cattle rustling, is another essential use that may be given to the invention both by the private sector and the state. It could even be the case that one of the purposes (sanitary or police) could be managed by the private sector and the other by the state.

It is noteworthy that this project benefits not only the early detection of Foot and Mouth Disease but it is also a key instrument to detect other type of diseases that are based on an increase in the animal's temperature, such as Brucellosis. This system can also be used to better control the cattle rustling, collaborate in the modernization of key sectors such as dairy, provide data on the physiological state, the estrous cycle, the pregnancy, and the prediction of birth. The system can detect these conditions by analyzing the data gathered by our sensors which can determine behavioural traits.

In addition and independently to the above, five further advantages are considered:

Even if there is not a rise in temperature a text message is sent at least three times per day (or the number of times that the customer or application demands it). Therefore, an important database is generated that provides vital information, create statistics (for example: the hike made by the animals, the grazing, the temperature variation by heat stress, the physiological state, the estrous cycle), etc.

This device can be implemented in other animals and not just in beef cattle.

The device as it is can be applied for other uses by changing and/or adding sensors. For example, it is possible to measure other parameters of the animal by adding sensors and then send that information along with the other data.

The device will be expanded and modified to be used for all sorts of applications.

The transparency that the device will provide will necessarily promote trade, especially international trade.

Brief Discussion of the Related Art

I will describe what is the state of the art and the invention nearest to mine, which I will describe first:

EP2446855 A1 (26 Oct. 2010). This application, even though being the closest one, presents serious differences with my own. It is primarily (or even only), a device to better determine the best moment for the insemination of a cow, it may be located only in its vagina and it has a battery. The main factor is that it is only applicable to cows in reproductive age, not for bulls, young animals of either sex or cows out of reproductive period. In the second place, it is only applicable to the vagina of a cow in reproductive age, not in any other place of the body. Additionally, the device may be used for only a relatively short period, as long as its battery lasts, and it does not provide the geographical coordinates where the animal is sited. Thus, which is the cow in question and where is it located is not information provided by this device. This invention would also be of nil value to fight cattle rustling. Also, it is not an autonomous invention, since it depends on a battery of finite energy, and is thus not continuous or indefinite in time. Its way of transmitting information is, additionally, radically different from mine, since I employ text messages through the cellular telephone network, and, as I said, this one does not transmit a GPS value.

It is not, thus, a valid antecedent to my invention.

US2004074448 (22 Apr. 2008). This patent is even less relevant to my invention, since it also refers to how to determine the fertile moment for the insemination of a cow, it is only used through vaginal insertion, it communicates with other cows' devices as well as with the base and serves basically for herd management. As in the previous invention, it refers only to bovine cattle, only to female cattle, and only in fertile period.

WO2008138076 (14 May 2008). This application refers to a intrauterine device, which automatically limits it to the female genre of the species, and one of its goals is the detection of changes in the intra-abdominal pressure coming from the diverse surrounding organs. Other goal of this invention is to determine the fertile moment of the cow, but not sicknesses or geographical location, and is therefore of nil value for the masculine portion of the cattle population, or that portion of the female population which is not in its reproductive age. It is also nil to fight cattle rustling, and is therefore not an antecedent to my invention.

BE1015962 (29 Mar. 2004). Most of my objections to the validity as antecedents that I have stated regarding the previous applications are applicable to this one too. This one refers to a device for detecting and reporting changes in the cervix or in the vagina of a cow. The device is inserted in the vagina and is used to measure expansion and contraction of the cervix canal. It includes a sensing wire, antennae, integrated (printed) circuit, rechargeable batteries and a load solenoid. It does not transmit the animals' temperature and position and is only valid for the female population in its reproductive period, being thus useless against cattle rustling.

DETAILED DESCRIPTION OF THE PREFERRED EMBODIMENTS

The Initiative

Business Concept

The overall objective is to create a tool for farmers, researchers and authorities, that enables them to know in real time the position of their animals and the vital signs that they want to monitor (eg. temperature) to prevent theft, loss of animals and/or epidemics in their animal population and also to better understand the behavior of the animals in order to improve the various cattle breeding processes within the different establishments.

The aim is to create a simple, low cost device, both in its implementation and in its annual maintenance, to be applied to the maximum number of animals, which increases the information on the possible occurrence of FMD or other disease. Its wide dispersion will be possible if the conditions of simplicity, reliability and low cost are fulfilled. At first there will be a slow development but there is no doubt that in the future their use of the device will be widespread as more farmers see its advantages, and it could even be that national authorities decide to make it compulsory. Moreover, the wide social impact is considered fundamental, since different regional sectors will be involved, and, will receive direct benefit from the invention.

It is undeniable that, after several national and regional disasters, there is a notorious perceived necessity of preempting epidemic outbursts, and that has defined my vision and my mission in developing this invention.

Vision

That through the project the whole world can acquire secure, fast and objective information regarding the occurrence of cattle diseases outbreaks.

Mission

To create a 24-hour-enabled system that allows the detection of any abnormality at any time and place in order to isolate the anomalies as soon as possible.

The Device

This project is completely innovative since there are no other current products or processes. It must be stated that this invention is based on the combination of multiple existing technologies, some of them used in a novel way, besides the novelty of the combination itself, with surprising results in its double role of preempting epidemic diseases and cattle rustling: the radiofrequency network such as the cellular network, the General Packet Radio Service (GPRS) modem, the Global Positioning System (GPS) receiver, the subcutaneous Radio Frequency Identification (RFID) temperature sensors, and other sensors. This makes it much easier to implement, since in most regions some or all of the components already exist.

Using bio-thermal technology the device measures the animal's temperature through a subcutaneous chip. The chip must be implanted in the retro auricular region, which is the best place to take the animal's temperature. This chip is also a microtransponder that transmits the information that it contains to an RFID transceiver. Therefore, the animal carries a collar that contains an RFID transceiver, which meets the corresponding International Standard Organization (ISO) standard, where the temperature measurement can be received and stored. There is also a Global Positioning System (GPS) receiver (or any other system for geographical positioning) and a General Packet Radio Service (GPRS) modem (or any other data system transceiver). A micro controller controls all these components. The information is sent in a text message, or the type that enables the technology available in the area, to the company's server and it contains the animal's identification and the animal's temperature measurement, which is obtained from the RFID transceiver, and the position coordinates, which are obtained from the GPS receiver. The content of the text message goes through a proprietary software program that processes the information and in case the temperature exceeds a certain threshold immediately triggers a visual and sound alarm.

All values received in the server are compared with a threshold number defined in the software application (this threshold number depends on the animal type and is determined based on outside animal health studies). If the temperature measurement is above the threshold the software platform creates a request for an SMS provider to send the text message to the telephone number of the farmer that the software platform has registered. In this SMS we inform the location and id of the animal, along with a warning message.

The animal location is also displayed on a map that can be seen by login into the company's website. The ability to detect high temperatures in an animal enables fast decision making by a highly qualified veterinarian team. In the company's computers the warning signal is seen in real time on a map specifying the location where the high temperature was detected. An informatics server facilitates in real time the sanitary/police control, thus creating its own database with information that can be processed using a proprietary information processing software.

It is noteworthy that the monitoring device is both animal-friendly and environmentally friendly. In order to power the electronic system there is a Lithium Polymer battery or a Lithium Ion battery rechargeable by a solar cell. The same is located in the outside of the collar. This makes the system completely autonomous without having to connect it to the power grid.

The device allows sending and receiving information from remote locations without being connected to the power grid and without the need to have personnel to manipulate the devices once placed in animals.

A wire is also attached to the whole length of the collar so that if the collar is opened or cut a message is sent to the company's server and to the ranch administrator's cell phone so appropriate action can be taken. Also, the system can detect if the animal is outside of the ranch premises and alert the ranch administrator.

The information is sent as many times as the application requires it. For example, to monitor diseases a message is sent 4 times per day, but if the temperature exceeds a certain threshold the information is sent immediately after the anomaly is detected.

The system allows the addition of other sensors to monitor other physiological parameters of the animal. The information recovered from those sensors can be transmitted together with the other information.

In addition, through a very easy to use web platform the farmer can monitor his livestock and access statistics, which are generated with all the information collected and stored in the data base, to improve his production.

The detection of sickness can be achieved by monitoring the animal's position and temperature, the distance walked in one day, the behaviour of one animal in comparison with the behaviour of the whole herd, and a rise in temperature can be symptoms of sickness.

In this document the animal refers to cattle, sheep, horses, or any animal that can have a collar placed around its neck. In this document the ranch administrator is the person in charge of the animals. In this document the ranch premises mean the area where the animals are located. This is a low cost system since most monitoring devices are over 1000 dollars. We achieve this by using off-the-shelf commercially available components.

Figure 1:
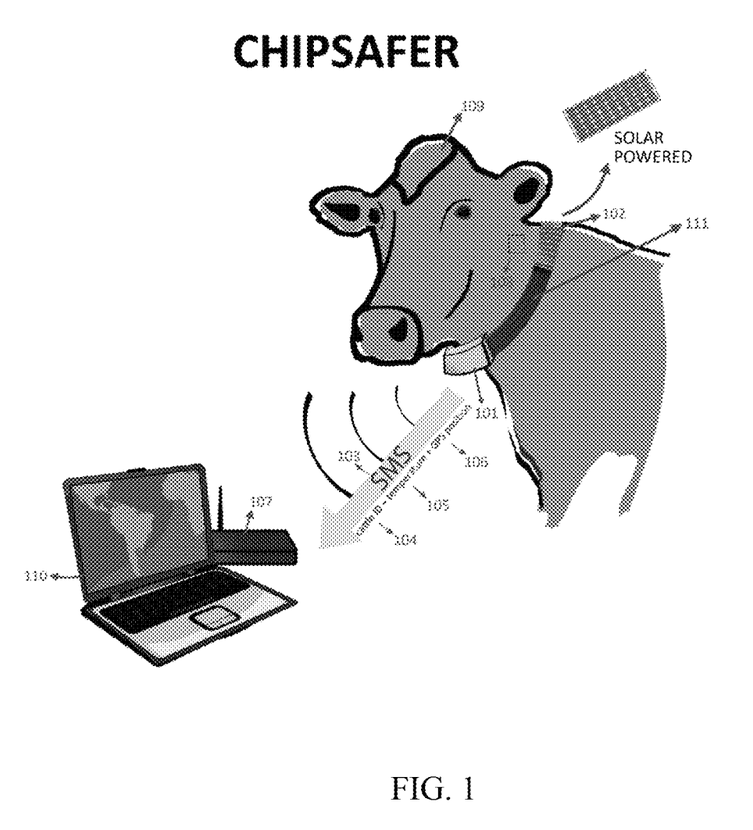
FIG. 1 is a diagram of the overall system illustrating the interaction between system components.

Regarding FIG. 1, the Chipsafer device, which consists of a collar 111 with a box that contains electronics inside 101, sends a text message, SMS 103, to the company's server 107 with the animal's identification (ID) 104, the temperature measurement 105 and the exact location of the animal 106 obtained using a GPS receiver. The Chipsafer device is powered using solar cells 102, which are attached to the collar. The Chipsafer device communicates through RFID with an implantable temperature sensor 108. From the company the information is sent to the customer. The Chipsafer device is placed on an animal 109, in this case the drawing shows a cow but it could be a sheep, a horse, or any other animal that could hold the Chipsafer device. The data is displayed on a website 110.

Figure 2:
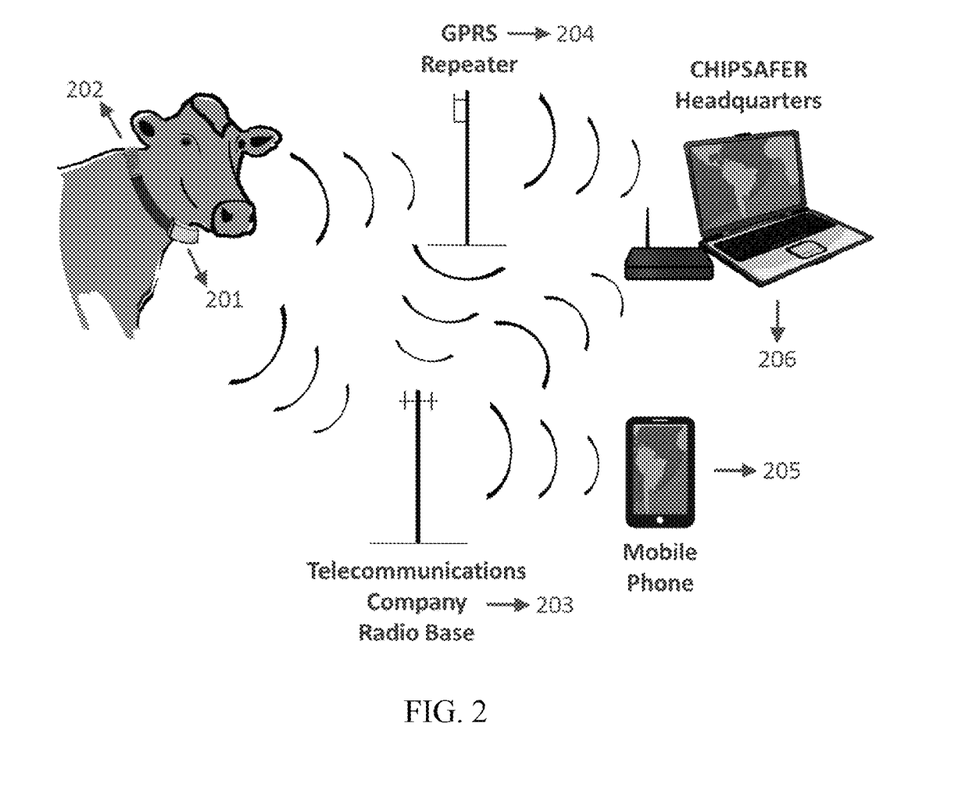
FIG. 2 is a diagram illustrating how the interactions between components in the system occur over a larger telecommunications infrastructure.

As shown in FIG. 2, the Chipsafer device 201 on animal 202 transmits the information to a GPRS repeater 204 or to a telecommunications company radio base 203. The information is then transmitted from the antennas to a mobile device 205 and to the company's server 206.

Figure 3:
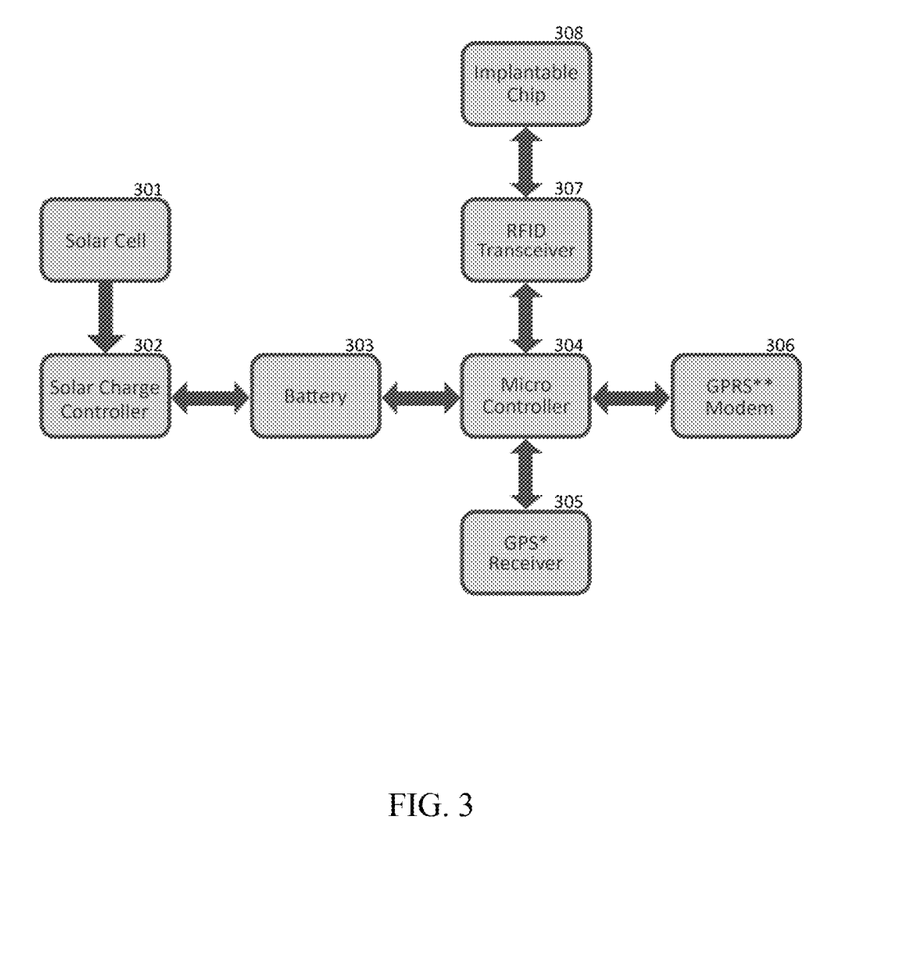
FIG. 3 is a diagram illustrating the elements of the monitoring device.

The diagram of FIG. 3 shows the Chipsafer system containing a microcontroller 304, a GPRS modem or any other data system transceiver 306, a GPS receiver or any other system for geographical positioning 305, a rechargeable battery 303, a solar charge controller 302, and a RFID transceiver 307. The whole system is powered by solar energy. A solar cell 301 is located attached to the collar and outside of the box. The implantable chip 308 communicates with the RFID transceiver 307. If other sensors are added they will communicate with the microcontroller.

Figure 4:
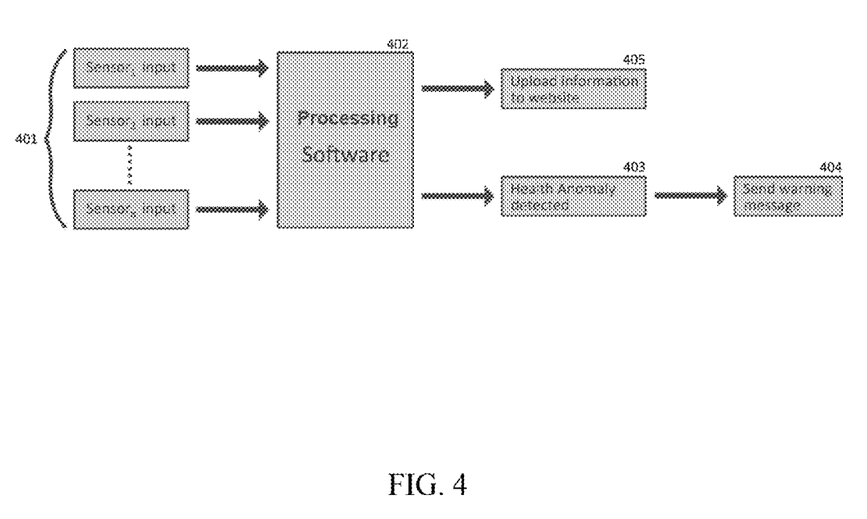
FIG. 4 is a diagram illustrating the process performed by the system server at headquarters.

The information gathered by an array of sensors 401 comprising different sensors which can include the implantable chip is processed by our software 402. As seen in the system diagram FIG. 4, the information is then uploaded to the website 405. Any user with a password can then access his information. In the event that an anomaly in the animal's health is detected 403 a message is sent to the ranch administrator 404.

Figure 5:
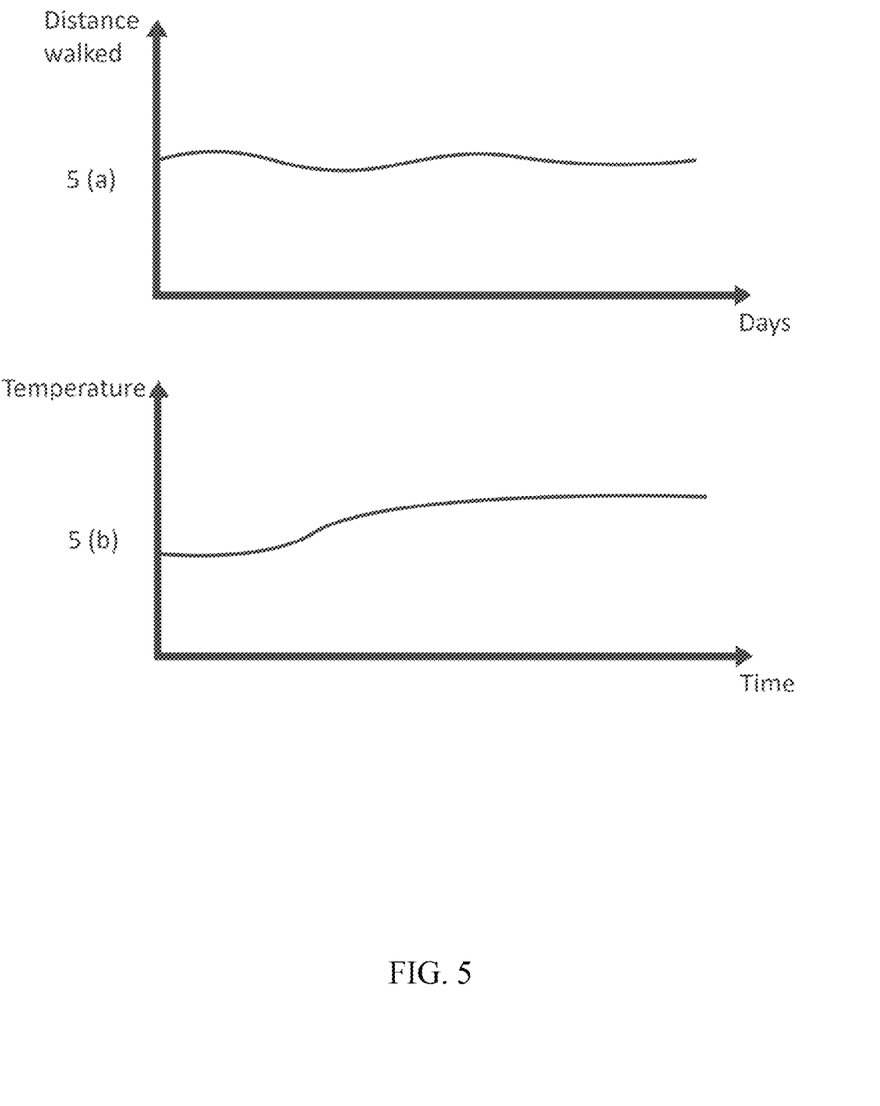
FIG. 5 is a graph illustrating example data from an animal or group of animals.

Examples of statistics generated by the software using the data gathered by the sensors are shown in FIG. 5. Specifically, the graph of FIG. 5(a) is the distance an animal walked per day, which is useful to know grazing habits. The graph FIG. 5(b) is of temperature measured in an animal through a period of time.

Figure 6:
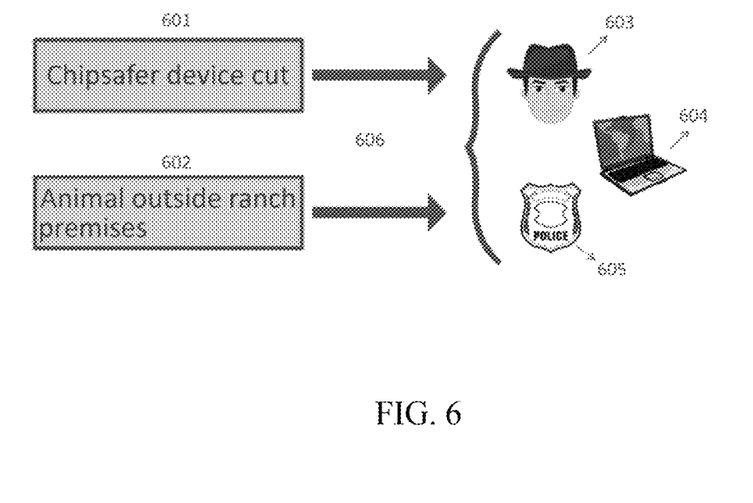
FIG. 6 is a diagram illustrating a reporting process performed by the system.

If the Chipsafer device is cut 601 a warning message 606 is sent to the ranch administrator 603 and to the authorities 605 as shown in FIG. 6. Also, this alarm can be visualized in the company's website in a map 604. If the animal goes outside of the ranch premises 602 a warning message 606 is sent to the ranch administrator 603 and to the authorities 605. Also, this alarm can be visualized in the company's website in a map 604.

Some not limiting characteristics of the invention include:
Method of monitoring the animal's temperature (or other physiological variables) through a sensor and a transmission collar, and of sending through a data message the temperature and geographical location of the animal (or object) and other data to an informatics central to facilitate in real time the health control, thereby creating a proprietary database that can be processed using a proprietary information processing software.
Device to be used according to the above-noted method, that comprises the following characteristics: tracking systems, radiofrequency networks, informatics systems, measurement sensors, power management, etc.
Method of detecting animal diseases that manifest through changes in the temperature.
Method that enables the detection of temperature changes in animals in an automatic, continuous and remote way.
System that enables the creation of a database with the animal's temperature, the environmental conditions, the animal's identification, the geographical coordinates, etc.
Low cost method.
Implementation This is a non-exclusive example of an implementation plan made for the Uruguayan case. The idea is to then expand it to the rest of the world. Being this device for continuous control at a distance, it will be even more useful the bigger the country is. Initially, a 24-hour a day monitoring office in the South region will be required. The office can be rented, and there will be personnel working 8 hour shifts (in the beginning no more than one employee per shift will be required, with back up personnel because of the existing law). The office will have administrative staff and computer technicians who will monitor the devices supported by veterinary technicians. Initially, there will be two 4×4 trucks that will go around the two regions into which the country will be divided. Later, when the scheduled conditions require it, there will be 4 more trucks and a new office in the North region. There will also be a specific maintenance department for repair and replacement of devices, collars, and other supplies. Furthermore, the project's original proprietary device design will be outsourced for manufacturing and will be ordered in quantities according to the need. A device will be placed in three out of every one hundred animals, but this ratio can vary according to the area and the proximity of the animals to each other and according to the application that the customer requires, for example, if what it Is wanted is to monitor the position of each animal then every animal must wear a collar. When the customer buys the devices and pays the monthly maintenance fee he also purchases an insurance for breakage of one every three devices per year. This insurance is included in the contract.

After the placement of the devices, the rural producers must pay a modest monthly fee to keep the system operational, maintain the contact with the company, and the system maintenance, among other things. It must be taken into account that the device is applied on a living creature, which makes it very dynamic. The animals are sent to slaughter or die because of different circumstances; therefore, a subcutaneous chip must be implanted in another animal while the collar can be reused.

The foregoing process will be possible because the office does not require high implementation costs. Regarding the components, support will be sought at the New Enterprises Sector of the National Bank [7] and at the National Corporation for the Development (CND) [8], who is eager to support such projects as mandated in the statutes of the CND. Significantly, this project would have support from international, technical, and financial organizations of the countries that import meat products, since the project fosters transparency in the handling of animal health issues. In terms of the success of the project, the goal is to have the system installed in at least all the developing world (it should be remembered how FMD dramatically affected Uruguay). Obviously, implementation in those countries would be based on the same principles.

Since this project is based on the utilization of radio frequency networks, at the same time there should be negotiations with the international telecommunications companies, with which mutual beneficial agreements must be reached. The cellular network operator benefits from this business because it generates data traffic where today it does not exist (as hypothetical case it is posed that only one percent of the head of beef cattle in Uruguay, on an estimated at the end of 2012 of approximately eleven million, use this system sending three text messages per day, it generates a new text messaging market to the telephony operator of about three hundred thousand new text messages daily).

Finally, this project involves the participation of professional technicians, such as agronomists, veterinarians, financial institutions, public offices, non-governmental organizations, and society as a whole. This project will definitely provide a solution to a very sensitive area. Moreover, given the past experiences, it is obvious the need that justifies this invention and gives its reason for being.

The Market

The target group includes all the agricultural sectors that, in the case of Uruguay geographically cover more than three-fourths of the territory [9]. These rural areas generally form the majority of a developing country's territory. Such countries will buy the device because it is an additional means of protecting animal health. Rapid detection of the disease in a region will help curtail its fast expansion in faraway areas with difficult access to information. The Unique Selling Point is very clear: no other product with similar characteristics exists. The costs for the buyer are reduced based on the enormous benefit that the same causes. It is added in this aspect the benefits at political level since it should be part of a good State policy. Furthermore, other big beneficiaries are the countries importing meat products. The perceived need, then, is multiple: covers small, medium and large livestock producers, the exporter countries and importing countries.

Marketing Strategy

The product should be simple and its entry into the market should focus on its two or three main characteristics and a single direct benefit as the basis of the campaign. The most accessible price is sought, since the objective is its massification. In the event that individual countries do not buy it, it must be accessible to the micro consumer market. Since the product is directed to large territorial extensions there is no specific site and its adaptation can be both general and comprehensive. The recommendations for Uruguay should be general and basic to place the project at a global level. Thus the advertising should be specific to the sectors involved (health, related professionals, farmers, government offices) through brochures, personal contact and use of social networks.

Based on this and alongside, a strategy of easy access to information will be implemented for the annual maintenance stages. For this there will be a team that will prioritize the personalization of the information to be delivered to the users with respect to structural factors, technological and application developments and improvements, general information, etc.

Given the impact that this activity will produce, it will certainly lead to the presence in mass media through interviews, news reports, and technical reports.

Social Purpose and Importance

From the point of view of the rural producer, the social and economic benefit will be undeniable because it generates more security on its activity. By decreasing the incident of FMD and its widespread transmittal it reduces the apprehension among the small producers and the wage earners, who are directly affected during the months that the epidemic lasts. In the case of the small producer, the benefits of the system are more extreme, since FMD could involve the death of a whole herd. The service sector also benefits, since it drives the micro economy in developing countries. The appearance of FMD decreases the country's activity, and in prolonged periods it can lead to recessions. From this it can be seen that it hurts the country since it has to do great efforts to balance the macro economy that has been damaged by a casual and accidental fortuitous event.

As stated in the Executive Summary, transparency is the critical factor in all-human activity and the social impact of the project will be enormous, embracing almost every sector within and outside a country's borders.

Thus, the perceived necessity of this invention is acutely felt, being this not only in developing countries but also in developed countries that import much of their beef and also have their very important cattle breeding activity.

Growth

The project's growth potential is enormous. Although the growth will be slow at first, it will be steady. In the medium-term, its growth will be exponential, as more and more producers, as well as government agencies, will be attracted by the advantages that this invention entails. Most important, this growth will result in greater social benefit.

Finance

In this section the Uruguayan case is considered as a non-exclusive example. Considering the recommended distribution of 3 devices for every one hundred cattle (in the case that the system will be used to monitor diseases), approximately 350,000 devices will be needed to cover a cattle population of over 11,000,000 animals. Such devices cost approximately US $190 (cost approximately no more than a couple of hundred dollars each, getting cheaper as the purchases increase and as there is worldwide production). From the beginning of the project the devices will be purchased gradually, according to market requirements.

The work will be divided in two stages:
a) Initial investment
b) Operational investment Regarding item (a) Table I shows that funds must be obtained in the Year 0. That is, prior to the market launch of the operational activities. This includes: the presentation before the national authorities, as well as public and private funding institutions; personnel recruiting; negotiating several contracts; and international negotiation efforts. The company will pursue tax exemptions (reduction in VAT rates on imports and sales of products in the domestic market, import tariffs and domestic excise tax).

In Item (b) the company would already be in the operational development until its normal activity. It was done for a five year period, which is considered sufficient for the project to be operational throughout the whole country, as shown in Table II.

Given the enormous social interest in the project, the necessary funding will be sought through the National Bank (Banco de la Republica Oriental del Uruguay) and through the National Corporation for Development (CND). Also, the company will pursue the support of international institutions that generally endorse projects of social interest, such as the Inter-American Development Bank and the World Bank.

Furthermore, as illustrated in Tables I and II, the financial needs are limited to Years 0 and 1 since the breakeven point will be obtained in Year 2, and the project would be completely self-sustaining from then on.

For all the reasons stated above, the funding that will be needed, which is detailed in the implementation plan, would correspond to a figure close to US $260,000, with part of the banking services included. As seen in Table II, the breakeven point would be reached in the first semester of Year 2. Therefore, the loan will be amortized and completely repaid within 36 months maximum. A credit line of up to US $500,000 should also be solicited to be exclusively dedicated to the import operations, at least, during Years 1 and 2.

As it was previously said, alongside all the above it will be negotiated the respective agreements and conventions with the telecommunications companies (such agreement is considered in the incomes for monthly maintenance in table II)

TABLE I

| Investment Costs (Year 0) | |
|---|---|
| Purchase of Device Samples | 32000 |
| Brochures | 12000 |
| Web Page | 2500 |
| Notary Expenses | 2900 |
| Per Diem | 2000 |
| Informatics Supplies | 3000 |
| 1 Veterinarian | 8000 |
| Personnel and Social Laws | 12000 |
| Publicity | 10000 |
| 2 4X4 Trucks | 51000 |
| Office Rent | 10000 |
| Total | 145400 |

Figures are expressed in United States Dollars 2012.

Figures are expressed in United States Dollars 2012 except for the item "Number of Devices", which is expressed in physical units. The selling price of each device would be of approximately US $210.

*Corresponds to a monthly fee of US $20 per establishment. This fee will increase in the case of facilities with more than, for example, 500 animals.

Implementation Plan

As stated in the previous section, the development of the project is specified in a clear chronology. Thus it can be seen that in Year 0 the focus will be on promoting and advertising the activities. At this time, detailed information on the project will be provided to the national authorities in order to obtain the appropriate authorization for the company's operation. It is also considered the administrative, technical and personnel needs that are required when any investment project. Table I show figures in the different items needed for this implementation. The project requires an operational office, two 4×4 trucks to go to the country's key points, accounting staff, a minimal of monitoring staff and a veterinarian.

Year 1 is particularly laborious because it requires everything needed in Year 0 plus effective and efficient implementation and operation. Revenues will be negligible in Year 1, because the major activities will be to implement the project administration and to generate stocks. The projects original device design will be outsourced for manufacturing to countries that specialize in this kind of manufacture. Therefore, the stocks are to be formed through a permanent import and according to the need of devices. It is important to clarify that Uruguay has a very fluid external trade with few obstacles to importing, especially when it is a project with a wide social interest. The unit costs of the devices include the tariffs and import taxes. Of course, the project will apply for the appropriate tax exemptions that are allowed based on the high degree of social interest, which

TABLE II

| | Investment Project | | | | | |
|---|---|---|---|---|---|---|
| | Year 1 | Year 2 | Year 3 | Year 4 | Year 5 | Total |
| Number of Devices Sales | 10000 | 50000 | 100000 | 150000 | 15000 | 325000 |
| Devices | 2100000 | 10500000 | 21000000 | 31500000 | 3150000 | 68250000 |
| Monthly Maintenance* | 240000 | 1440000 | 3840000 | 7440000 | 7800000 | 20760000 |
| Total Income | 2340000 | 11940000 | 24840000 | 38940000 | 10950000 | 89010000 |
| Cost of Sales | | | | | | |
| Devices | 1900000 | 9500000 | 19000000 | 28500000 | 2850000 | 61750000 |
| Maintenance | 380000 | 1805000 | 3705000 | 6555000 | 6840000 | 19285000 |
| Maintenance (personnel) | 9600 | 19200 | 27800 | 27800 | 29800 | 114200 |
| Rents | 15000 | 27000 | 27000 | 40000 | 40000 | 149000 |
| Professional Fees | 12000 | 24000 | 24000 | 36000 | 36000 | 132000 |
| Salary base jobs | 45000 | 69000 | 69000 | 69000 | 45000 | 297000 |
| Social Contributions | 13950 | 21390 | 21390 | 21390 | 13950 | 92070 |
| Administration Expenses | 9900 | 11200 | 14200 | 14800 | 14800 | 64900 |
| Advertising | 45000 | 32000 | 24000 | 24000 | 12000 | 137000 |
| Sub-total | 2430450 | 11508790 | 22912390 | 35287990 | 9881550 | 82021170 |
| Income Tax | 0 | 107802.5 | 481902.5 | 913002.5 | 267112.5 | 1769820 |
| Total Expenditures | 2430450 | 11616592.5 | 23394292.5 | 36200992.5 | 10148662.5 | 83790990 |
| Total | −90450 | 323407.5 | 1445707.5 | 2739007.5 | 801337.5 | 5219010 | would result in a substantial reduction in the cost and consequently, a reduction in the selling price. Furthermore, the monitoring staff will be increased and another veterinarian must be hired.

In Year 2 the administrative component is organized and operational throughout the country. Furthermore, the devices imported each year will be sold immediately, and this process will continue from Year 3 onward. In this case three more 4×4 trucks will be purchased and two additional veterinarians will be hired. Then, the country will be divided into four regions, each of them having its own office as an operational base; therefore, the respective premises will be rented in the most convenient place.

It is significant that, since the project is based on technological devices, a primary and basic element for the viability of the entire project is the maintenance and update, which can be seen in the respective item in Table II. The figures in this item increase according to the devices in circulation, and tend to remain constant with the passing of time. In the user contract a period of insurance at the company's expense will be specified and separate from the maintenance for malfunction, or manufacturing defects. Obviously, this cost includes not only the devices but also the personnel that will be in charge of repairing them.

Throughout this work, the business will be the monthly maintenance, rather than the sale of the devices since the goal is to keep the cost for the farmer as lower as possible to fulfill the planned objectives.

With the medium or long-term application of this project—subject to its widespread implementation—the eradication of FMD becomes a realistic outcome. The real-time detection and the immediate location of the outbreak mean that the disease can be researched at an early stage to determine the causes of the outbreak. This research, together with the use of statistics, will enable the company to keep optimal control of the areas where the disease is most likely to become endemic, leading to risk reduction, and even to eradication of the disease. This in no way prejudices the commercial aspect of the project, since its initial investment costs are amortized over a short time, and the earnings are direct in subsequent years. Moreover, even in the case of disease eradication, the monitoring should persist.

Finally it should be taken into account that the country itself might decide to perform the administration, advertisement, and placement of the devices; in that case the company's activity would be limited to providing the appropriate devices. Only costs and sales would be handled by the company, plus administrative costs. This possibility should be taken into account but it would not be elaborated in this document. The investment cost of Year 0 would be the same, while in the following years the same criteria as the one used in Table II would apply. Also, the credit line might vary because of the likelihood that the devices will be purchased in bulk.

The invention claimed is:

1. A method for detection and control of animal sickness or theft, comprising:
   measuring physiological parameters of an animal as animal specific data with at least one sensor embedded in the animal, including a subcutaneous chip implanted in a retro-auricular region of the animal;
   transmitting the physiological parameters to an electronic collar including at least one transceiver, a renewable-energy power system, and a wire extending along the whole length of the electronic collar, wherein the renewable-energy power system recharges autonomously;
   detecting and transmitting the physiological parameters including internal body temperature data to an informatics server, wherein the detection is automatic, autonomous, and continuous;
   detecting and transmitting a geographical location of the animal to the informatics server, wherein the detection and transmission of the geographical location is automatic, autonomous, and continuous;
   sending a first emergency message to the informatics server and to a cellular phone, if the wire in the electric collar is cut, indicating that the animal may be stolen;
   sending a second emergency message to the informatics server and to the cellular phone if the animal is outside of a fixed predetermined area;
   sending, via an SMS message over a data connection, the animal specific data including internal body temperature data, individual animal identification, and geographical location to the informatics server to display the animal specific data in real time to a user;
   creating a database of the animal specific data that can be processed to generate statistics;
   transmitting, from the informatics server, the statistics and alerts to authorities to facilitate, in real time, sanitary control;
   providing a web-based platform to the user for viewing the animal specific data, the statistics and the alerts in the database;
   providing a display to private personnel to view the alerts from all electronic collars transmitting to the informatics server;
   comparing the animal specific data to the statistics to detect foot-and-mouth disease in the animal; and
   sending a third emergency message to the cellular phone, if foot-and-mouth disease is detected.

2. The method according to claim 1, further comprising: detecting sickness through changes in the internal body temperature data of the animal.

3. The method according to claim 1, wherein the database includes the internal body temperature and the physiological parameters of the animal, environmental conditions, the individual animal identification, geographical coordinates, and movement of any number of animals.

4. The method according to claim 1, further comprising: analyzing the database to provide information on sickness, caloric stress and other conditions the animal must endure and which may affect the internal body temperature data or other physiological parameters, geographical positions and grazing habits, and a physiological state.

5. The method according to claim 1, wherein the physiological parameters allow monitoring of an estrous cycle, a pregnancy, and birth for a female animal without any vaginal or genital transmitter or sensor insertion.

6. The method according to claim 1, including at least one of the following elements: a monitoring and localizing system, a radio frequency network, a cellular phone system, information technology systems, and power management systems allowing autonomous and continuous functioning without the need of being connected to a power grid.

7. The method according to claim 1, further comprising: sending the physiological parameters in the animal together with the geographical location of the animal.

8. The method according to claim 1, further comprising: creating statistics with the animal specific data recovered and stored in the database over time, the animal specific data, environmental conditions, and a physiological state; and
   sending these statistics to a customer.

9. The method according to claim 1, wherein the renewable-energy power system includes batteries and solar cells.

10. The method according to claim 1, wherein foot-and-mouth disease is detected if a predetermined internal body temperature threshold is reached.

11. The method according to claim 1, wherein the electronic collar is autonomous without any need for physical user access.

12. The method according to claim 1, wherein the informatics server displays the geographical location of a sick or stolen animal on a map.

13. The method according to claim 1, wherein the data connection is a general packet radio system.

14. An animal monitoring system, comprising:
   at least one radio frequency identification (RFID) tag disposed subcutaneously in an animal in a retro-auricular region of the animal;
   an electronic device disposed on a collar, the electronic device comprising:
      at least two transceivers, a first transceiver connected to the at least one RFID tag and a second transceiver connected to a telecommunications base station;
      a GPS receiver providing a geographical location of the animal;
      a wire extending along the whole length of the collar and connected to the electronic device; and
      a solar panel providing power to the electronic device, the electronic device being autonomous such that external power and regular user access are not needed;
   an informatics server, including a database, connected to the telecommunications base station and receiving animal specific data including internal body temperature, individual animal identification, and geographical location in real time;
   a first display providing a web-based platform to a customer to view the animal specific data and statistics in a database;
   a second display allowing private personnel to view the database, the statistics, and alerts from all electronic collars transmitting to the informatics server;
   a third display allowing government viewing of the alerts; and
   a cellular phone connected to the telecommunications base station and receiving emergency messages,
   wherein if the wire in the electric collar is cut, the informatics server transmits a first emergency message to indicate theft of the animal, wherein if the animal is outside of a fixed, predetermined area, the informatics server transmits a second emergency message, wherein the animal specific data is transmitted to the informatics server via SMS messages, each SMS message including at least the individual animal identification, the internal body temperature and the geographical location,
   wherein the informatics server processes the animal specific data in the database to generate the statistics, wherein the informatics server compares the animal specific data to the statistics to detect foot-and-mouth disease in the animal, and the informatics server sends a third emergency message to the cellular phone, if foot-and-mouth disease is detected.

* * * * *